United States Patent [19]

Collen et al.

[11] Patent Number: 5,336,495
[45] Date of Patent: Aug. 9, 1994

[54] USE OF STAPHYLOKINASE FOR THE PREPARATION OF A PHARMACEUTICAL COMPOSITION FOR TREATING ARTERIAL THROMBOISI

[75] Inventors: Désiré J. Collen, Schoonzichtlaan 20, B-3020 Winksele-Herent; Jean-Marie Stassen, Wilsele; Henri R. Lijnen, Herent, all of Belgium

[73] Assignees: Leuven Research & Development vcw; Désiré J. Collen, Belgium

[21] Appl. No.: 91,885

[22] Filed: Jul. 14, 1993

Related U.S. Application Data

[63] Continuation of Ser. No. 760,343, Sep. 16, 1991, abandoned.

[30] Foreign Application Priority Data

Jun. 28, 1991 [EP] European Pat. Off. ......... 91201670.6

[51] Int. Cl.$^5$ .................................... A61K 37/547
[52] U.S. Cl. ................................... 424/94.64
[58] Field of Search ........................... 424/94.64

[56] - References Cited

FOREIGN PATENT DOCUMENTS 245444 5/1987 Denmark .
0337817 10/1989 European Pat. Off. .

OTHER PUBLICATIONS

Matsuo et al., Blood 76(5): 925–929 (1990).
Itoh, CA99:16311 (1983).
Abstract: JP-A-61 219 382, Sep. 29, 1986.
Abstract: JP-A-59 135 888, Aug. 4, 1984.
Friedman et al., "The Pathogenesis Of A Coronary Thrombus," vol. 48, No. 1, pp. 19–44 (1966).
Davies et al., "Plaque fissuring–the cause of acute myocardial infarction, sudden ischaemic death, and crescendo angina," Br. Heart F., vol. 53, pp. 363–373 (1985).
Jang et al., "Differential Sensitivity of Erythrocyte-Rich and Platelet-Rich Arterial Thrombi to Lysis With Recombinant Tissue-Type Plasminogen Activator," Circulation, vol. 79, No. 4, pp. 920–928 (1989).
Yasuda et al., "Lysis of Plasminogen Activator-Resistant Platelet-Rich Coronary Artery Thrombus With Combined Bolus Injection of Recombinant Tissue-Type Plasminogen Activator and Antiplatelet GPIIb/IIIa Antibody," JACC, vol. 16, No. 7, pp. 1728–1735 (1990).

*Primary Examiner*—Douglas W. Robinson
*Assistant Examiner*—Jean Witz
*Attorney, Agent, or Firm*—Webb Ziesenheim Bruening Logsdon Orkin & Hanson

[57] ABSTRACT

The present invention relates to the use of staphylokinase for the preparation of a pharmaceutical composition for treating arterial thrombosis, such as e.g. myocardial infarction. It is demonstrated that staphylokinase can be particularly useful as a thrombolytic agent for the lysis of platelet-rich clots. Furthermore it is demonstrated that staphylokinase, unlike streptokinase, does not induce antibody induction upon repeated administration.

3 Claims, 3 Drawing Sheets

USE OF STAPHYLOKINASE FOR THE PREPARATION OF A PHARMACEUTICAL COMPOSITION FOR TREATING ARTERIAL THROMBOISI

This is a continuation of copending application Ser. No. 07/760,343 filed on Sep. 16, 1991, now abandoned.

The invention relates to the use of staphylokinase for the preparation of a pharmaceutical composition for treating arterial thrombosis. More in particular it relates to the use of staphylokinase for the preparation of a pharmaceutical composition for treating myocardial infarction.

Thrombotic complications of cardiovascular diseases are a main cause of death and disability and, consequently, thrombolysis could favorably influence the outcome of such life-threatening diseases as myocardial infarction, cerebrovascular thrombosis and venous thromboembolism. Thrombolytic agents are plasminogen activators that convert plasminogen, the inactive proenzyme of the fibrinolytic system in blood, to the proteolytic enzyme plasmin. Plasmin dissolves the fibrin of a blood clot, but may also degrade normal components of the hemostatic system and induce the so-called lyric state. Physiological fibrinolysis however is fibrin-oriented as a result of specific molecular interactions between plasminogen activator, fibrin, plasmin(ogen) and $\alpha_2$-antiplasmin.

One of the thrombolytic agents currently used in therapy is streptokinase. Streptokinase is a $M_r$ 45,000 protein secreted by $\beta$-hemolytic streptococci It is used in thrombolytic therapy, but its administration is associated with extensive systemic fibrinogen breakdown. Its efficacy for coronary thrombolysis in patients with evolving acute myocardial infarction is limited, amounting to approximately 50 percent coronary artery recanalization within 90 minutes. Exposure to streptokinase provokes allergic reactions in about 5 percent of treated patients and consistently induces specific antibody formation which precludes its repeated use within several months. Furthermore, streptokinase antibodies may promote platelet activation and thromboxane production, which may limit its thrombolytic potency.

It has now been found that staphylokinase is a potent thrombolytic agent towards platelet-rich clots, found for example in patients with platelet-rich arterial thrombotic disease, including evolving acute myocardial infarction. Experiments in baboons and dogs showed that no preexisting antibodies could be demonstrated for staphylokinase nor induction of neutralizing antibodies following intravenous administration.

In a hamster pulmonary embolism model it was demonstrated that staphylokinase was more efficient towards clots containing 1,500,000 platelets per $\mu l$ than streptokinase. Furthermore it was demonstrated in dogs that at the arterial side recanalization with staphylokinase was more rapid, more frequent and more persistent than with streptokinase.

The present invention thus demonstrates that staphylokinase can be a practical alternative thrombolytic agent to streptokinase, without the undesirable side effects of the latter.

Pharmaceutical compositions, containing staphylokinase as the active ingredient, for treating arterial thrombosis in human or veterinary practice may take the form of powders or solutions and may be used for intravenous, intraarterial or intramuscular administration. Such compositions may be prepared by combining (e.g. mixing, dissolving etc.) the active compound with farmaceutically acceptable excipients of neutral character (such as aqueous or non-aqueous solvents, stabilizers, emulsifiers, detergents, additives), and further, if necessary with dyes. The concentration of the active ingredient in a therapeutical composition may vary widely between 0.1% and 100%, dependent on the character of the disease and the mode of administration. Further the dose of the active ingredient to be administered may vary between 0.05 mg and 10 mg per kg of body weight.

The present invention will be demonstrated in more detail in the following examples, that are however not intended to be limiting to the scope of the invention.

EXAMPLE 1

Figure 1A:
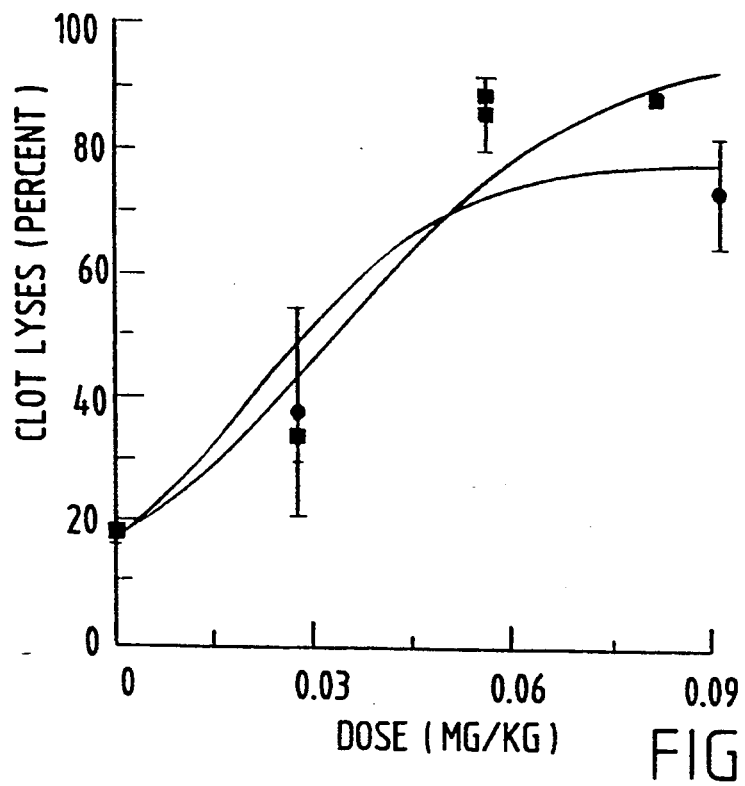
FIGS. 1A and 1B are line graphs which compare the thrombolytic potency of staphylokinase and streptokinase in hamsters having pulmonary emboli.

Thrombolysis of platelet-rich and platelet-enriched human plasma clots in the hamster pulmonary embolism model Evaluation of the thrombolytic potency of staphylokinase and streptokinase towards platelet-rich human plasma clots in vivo was performed using the pulmonary embolism model in the heparinized hamster as described in Stassen, J. M. et al., Fibrinolysis 4 (Suppl 2), 15–21, 1990.

Platelet-rich clots were prepared either from fresh platelet-rich human plasma (platelet count $3 \times 10^5/\mu l$) or from platelet-enriched human plasma (platelet count $1.5 \times 10^6/\mu l$) containing traces of $^{125}$I-labeled fibrinogen. Plate-let-rich human plasma was obtained from 10 ml samples of fresh blood collected on acid-citrate-dextrose by centrifugation for 10 min. at 100 g. The platelet-rich supernatant plasma (approximately 3 ml) was removed and centrifuged for 2 min. at 500 g to obtain a platelet pellet. The platelet pellet was resuspended in 200 $\mu$platelet-poor ACD plasma, obtained from blood centrifuged for 5 min. at 1,000 g. The platelet count of the resuspended platelet pellet was determined and adjusted with platelet-poor citrated plasma to a platelet count of 300,000/$\mu l$ (platelet-rich plasma) or 1,500,000/$\mu l$ (platelet-enriched plasma).

A 50 $\mu l$ $^{125}$I-fibrin labeled human platelet-rich or platelet-enriched plasma clot was produced in vitro as described above and injected into the jugular vein of heparinized outbred hamsters. Staphylokinase or streptokinase were infused intravenously over 60 min. and lysis was measured 30 min. after the end of the infusion as the difference between the radioactivity initially incorporated in the clot and the residual radioactivity in the lungs and the heart. Fibrinogen and $\alpha_2$-antiplasmin levels in plasma from blood samples taken at the end of the experiment were determined as described in Clauss A., Acta Haemat. 17, 237–246, 1957; and Edy J. et al., In: Progress in Chemical Fibrinolosis and Thrombolysis. Davidson J. F. et al., eds. Vol 3. Raven Press, New York, 315–322, 1978.

The thrombolytic potency of the agents (percent clot lysis versus dose of compound administered per kg body weight) in the hamster venous thrombosis model was determined as follows. The values of the percent lysis versus dose in mg/kg were fitted with an exponentially transformed sigmoidal function:

$$y = \frac{100c}{1 + e^{-a(ex - eb)}}, \text{ using the statistical}$$

program GraFit (Erithacus Ltd., Middlessex, UK). This program allows to determine the following parameters: maximal lysis achieved, in percent (c); dose, in mg compound administered per kg body weight, at which the rate of clot lysis is maximal (b); maximal rate of clot lysis, in percent lysis per mg compound administered per kg body weight $$\left( z = \frac{ac}{4} \cdot e^b \right).$$

These parameters were obtained as mean ± SEM and the significance of the differences between these parameters was determined using Student's t-test. In order to convert the relative potency parameters determined on a gravimetric base to molar amounts based on a molecular weight of 45,000 for streptokinase and 15,500 for staphylokinase, the b values of staphylokinase, relative to those of streptokinase have to be multiplied with a factor 3 and the z values divided by a factor 3.

The relative thrombolytic potency of the compounds (percent lysis per mg compound administered per kg body weight) was also expressed in the following way. The individual dose-response data (percent lysis versus dose in mg/kg) were corrected for background lysis and the corrected data were fitted with a linear regression line forced through the origin. The significance of the differences between the regression line slopes was determined using Student's t-test. The results are summarized in Table 1. For comparison, results obtained with platelet-poor human plasma clot are also included. These results will be reported in detail elsewhere (Lijnen et al., Thromb. Haemost., in press).

Table 1 shows that in hamsters with platelet-rich human plasma clot in the pulmonary artery 25 experiments with saline infusion yielded a value for spontaneous lysis at 90 min. of 18±2 percent (mean±SEM). Fibrinogen levels at the end of the experiment were 160±13 percent of the baseline value and $\alpha_2$-antiplasmin levels were 95±5 percent. With staphylokinase, lysis at 90 min. after the start of the infusion in groups of 3 hamsters increased from 38±17 percent with 27 μg/kg to 75±9 percent with 90 μg/kg. Streptokinase at a dose of 27 μg/kg resulted in 34±4 percent lysis at 90 min., whereas a concentration of 80 μg/kg caused 90±1 percent lysis. In hamsters with a platelet-enriched human plasma clot in the pulmonary artery, 5 experiments with saline infusion yielded a value for spontaneous lysis at 90 min. of 19±4 percent (mean+-SEM). Fibrinogen levels were 110±15 percent of baseline and $\alpha_2$-antiplasmin were 140±33 percent of baseline. With staphylokinase, lysis at 90 min after the start of the infusion increased from 23±3 percent with 27 μg/kg to 88±1 percent with 160 μg/kg. Streptokinase at a dose of 80 μg/kg resulted in 30±4 percent lysis and at a dose of 500 μg/kg in 69±11 percent lysis Fibrinogen and $\alpha_2$-antiplasmin levels did not decrease significantly after infusion of staphylokinase or streptokinase.

Fitting of the dose-response data with the exponentially transformed sigmoidal function yielded values of z (maximal rate of clot lysis), b (dose at which maximal lysis occurs) and c (maximal lysis achieved), as summarized in Table 1. The thrombolytic potency of staphylokinase towards human plasma clots did not change with increasing platelet number. Although the potency of streptokinase towards plate-let-poor and platelet-rich clots was comparable to that of staphylokinase (on a weight base), streptokinase had a markedly reduced reactivity towards platelet-enriched plasma clots.

Figure 1B:
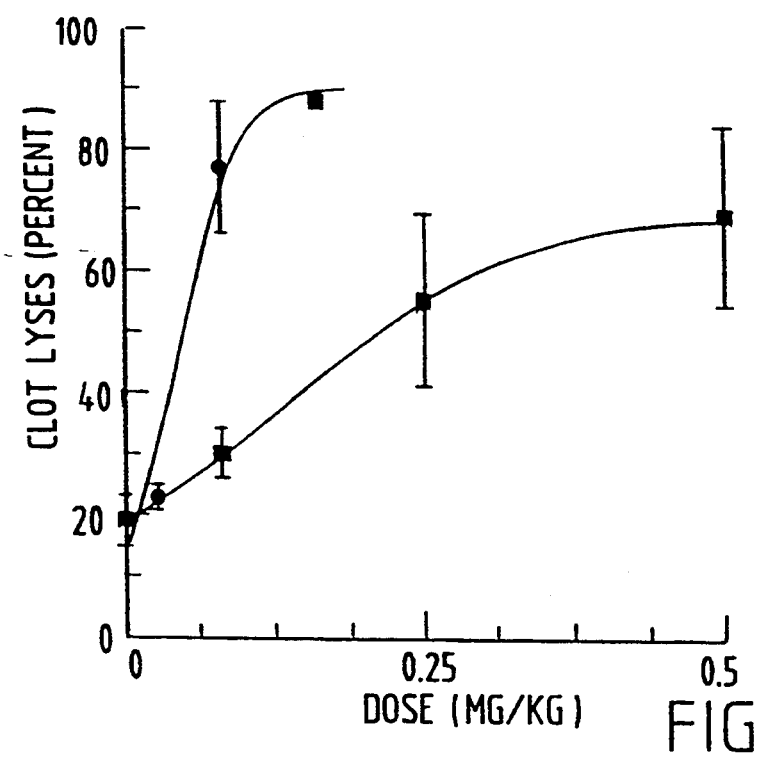

The results are also represented in FIG. 1, showing thrombolytic potency (percent lysis per mg/kg compound infused) of staphylokinase ( ) and streptokinase (■) in hamsters with pulmonary embolism consisting of a plate-let-rich plasma clot (300,000 platelets/μl) (panel A) or of a platelet-enriched human plasma clot ( 1,500,000 platelets/μl) (panel B). The data represent mean±SEM, as summarized in Table 1 and are fitted with the function $$y = \frac{100c}{1 + e^{-a(ex - eb)}}$$

Linear regression analysis of the data, confirmed the significantly reduced thrombolytic potency of streptokinase, but not of staphylokinase towards platelet-enriched plasma clots (data not shown).

EXPERIMENT 2

Thrombolysis in dogs with a combined femoral vein blood clot and a platelet-rich femoral arterial eversion graft thrombus The arterial thrombosis model was modified from a rabbit femoral arterial eversion graft thrombosis model as described in Jang, I. K. et al., Circulation 79, 920–928, 1989. Adult mongrel dogs weighing 10 to 20 kg were premedicated with 0.25 mg/kg fluanisone intramuscularly, anesthetized with 30 mg/kg intravenous sodium pentobarbital followed by 60 mg boluses when needed, intubated and artificially ventilated. Cefacidal (1 g) was given intravenously. Catheters were inserted in the left jugular vein for blood sampling and in the brachial vein for infusion of drugs. The left carotid artery was exposed and isolated. A 3 cm segment of the left carotid artery was then excised, everted inside-out, and immersed in physiologic saline. The left carotid artery was then cannulated for continuous blood pressure monitoring. The right femoral artery was exposed in the inguinal region and side branches, when present, were ligated. The baseline blood flow in the right femoral artery was measured with an electromagnetic flow probe (Medelad, Deurne, Belgium). The everted segment from the left carotid artery was then inserted into the transsected femoral artery by end to end anastomosis using 12 to 16 interrupted sutures with 7-0 nylon (DG Atraumatic ®, American Cyanamid Co , Danbury, CT). The microvascular clamps occluding the proximal and distal ends of the transsected artery were then released. The everted segment was allowed to thrombose and the stability of the occlusion thrombus was monitored for 1 hour. The surgical procedure was carried out under sterile conditions. The recanalization time, taken as the time from the start of the infusion of thrombolytic agent or placebo until reflow of the occluded graft segment, was determined with the electromagnetic flow probe. The blood flow was continuously recorded during 3 hours to document reocclusion or stable reflow.

The venous blood clot was produced in the left femoral vein, as described in Korninger C. et al., Clin. Invest. 69, 573–580, 1982. Briefly, the femoral vein was isolated between the inguinal ligament and the distal bifurcation and all side branches were carefully ligated, except for a predominant musculocutaneous branch, which was cannulated. After introduction of a woolen thread in the lumen, a 4 cm segment of the femoral vein was isolated between two vessel clamps, emptied and flushed with saline via the side branch catheter. The segment was then filled with a mixture of a trace amount of $^{125}$I-labeled human fibrinogen, 0.6 to 1.2 ml of fresh blood and 2 units of a thrombin solution. The venous vessel clamps were released after the right femoral artery clot was stabilized for 60 min, and the infusion protocol was started approximately 1 minute later. The radioisotope content of the venous clot was calculated by subtracting, from the original amount of $^{125}$I injected into the isolated vein segment, the radioisotope that was adsorbed on the cotton swabs placed around the vein segments, and radioiodine that was washed out from the thrombus into the blood stream, as determined 1 minute after removal of the clamps. Two hours after the start of the infusion of thrombolytic agent or placebo, the thrombosed segment of the femoral vein was ligated at both sides, removed, and its radioisotope content measured. The degree of clot lysis was determined as the residual radioactivity in the vein segment and expressed in percent of the radioactivity originally incorporated in the clot. An isotope recovery balance was expressed by comparing the sum of the total blood radioactivity at the end of the experiment (multiplied by three for extravascular distribution) and the radioactivity in the recovered thrombus, with that originally present in the clot.

All animals received intravenous bolus injections of heparin (100 U/kg per hour for 3 hours) starting just before the release of the right femoral artery vessel clamps and of aspirin (5 mg/kg) 10 min before the start of the infusion of thrombolytic agent. Thirteen dogs with stable arterial graft occlusion for 60 min were assigned to infusion of 16 to 32 µg/kg staphylokinase or to 250 to 500 µg/kg streptokinase. Five additional dogs, given heparin and aspirin but no thrombolytic agent, were also studied as controls.

During the experiments a rectally controlled heating pad was used to keep the body temperature at 37.5° C. Blood gas values were routinely checked. In some dogs selected for follow-up studies all catheters were withdrawn one hour after the end of the infusion and the wounds were sutured. When spontaneous respiration had returned, the trachea tubes were removed and the animals were returned to their cages. To maintain hydration, 500 ml of 0.9 percent NaCl solution and 100 ml of 5 percent glucose were infused before closing the wounds.

Template bleeding times were measured before and at 60 and 120 min after injection of study drugs. The bleeding time incision was made using an automated spring-loaded device (Simplate-II, General Diagnostics, Morris Plains, NJ) applied to the volar surface of the foreleg. The region of the incision site was washed, shaved and dried before performance of the first bleeding time. Blood samples were collected on citrate (final concentration 0.11 M) before, 10, 30, 60 and 120 min after the start of the infusion protocol, and at 24 hours. These samples were used for measurements of platelet count and ex vivo platelet aggregation induced with ADP (approximately 20 µM as individually titrated) and the combination of epinephrine (approximately 10 µM) and arachidonic acid (0.5 mM). Plasma was obtained for immediate determination of the fibrinogen level and stored frozen for subsequent determination of $\alpha_2$-antiplasmin and activated partial thromboplastin time. Platelet counting was performed on an automatic cell counter (Sequoia Turner Corporation, Mountain View, CA). Platelet aggregation was performed within one hour after blood sampling, using a standard aggregometer (Chronolog Corporation, Hayertown, PA). Fibrinogen and $\alpha_2$-antiplasmin were measured as described in Stassen J. M. et al., Fibrinolysis 4 (Suppl 2), 15–21, 1990, and the activated partial thromboplastin time by routine laboratory assay.

The significance of the differences in arterial patency between groups were compared using Fisher's exact test for categorical data or Student's t-test for paired or unpaired values. A Kruskal-Wallis non-parametric analysis of variance was performed on ranks of the ordered variable of femoral arterial patency, which ranges from 0 = persistent occlusion, 1 = cyclic reocclusion and reflow following initial recanalization to 2 = persistent patency following initial canalization, as determined with the electromagnetic blood flow probe. This form of analysis of variance was selected because of the Non-Gaussian distribution of the patency state variables.

The results of femoral arterial blood flow measurements after the insertion of the everted carotid artery segment into the transsected femoral artery are summarized in Table 2. In all of 18 dogs, blood flow was restored after release of the vessel clamp and stabilized at 20 to 32 percent of baseline. Graft occlusion, persisting for 60 min occurred in all dogs, within 30 min.

In 5 control dogs given aspirin and heparin but no thrombolytic agent arterial occlusion persisted throughout the observation period. Infusion of staphylokinase at a dose of 32 µg/kg in 3 dogs and 62 µg/kg in 1 dog was associated with reflow in all dogs with a time to recanalization of 36±9 min and this was followed by persistent patency in all animals. Infusion of staphylokinase at a dose of 16 µg/kg in 3 dogs produced recanalization within 30±3 min, with brief periods of subsequent reocclusion and reflow in two animals. Infusion of streptokinase at a dose of 500 µg/kg in 3 dogs was associated with reflow in 2 dogs and this was followed by persistent patency in 1 animal whereas a dose of 250 µg/kg in 3 dogs produced reflow within 97±3 min but this was followed by cyclic reocclusion and reflow in all animals.

Statistical analysis of the femoral arterial blood flow and venous clot lysis data showed no difference between the two groups given staphylokinase nor between the two groups given streptokinase. The data obtained with the two doses of each drug were therefore combined for further comparison. The time to reflow was significantly longer in the streptokinase groups than in the staphylokinase groups (p=0.006). A Kruskal-Wallis analysis with patency status ordered in the sequence of persistent occlusion (PO), cyclic reocclusion and reflow after initial recanalization (CR) and persistent patency after initial reflow (PP), yielded a p value of 0.016 for the difference between the combined staphylokinase and the combined streptokinase groups. The heart rate and blood pressure were not significantly different between the groups (data not shown).

The results of femoral vein clot lysis and isotope recovery are also summarized in Table 2. In the 5 control dogs given aspirin and heparin but no thrombolytic agent, the extent of apparant clot lysis was 23±6 percent, with a calculated isotope recovery balance of 86±6 percent. In the groups given 16 or 32 µg/kg staphylokinase, the extent of clot lysis was 79 ±10 and 92 ±3 percent respectively, as compared to 71±6 and 81±6 percent lysis in the groups given 250 or 500 µg/kg streptokinase respectively. The difference between the staphylokinase and streptokinase groups was not significant (p=0.20). The calculated isotope recovery balance ranged between 86 and 108 percent in all groups.

In aggregate, the results obtained with staphylokinase and streptokinase in the dog indicate that the thrombolytic potency of staphylokinase, on a molar basis, is at least five times higher than that of streptokinase. More importantly however, at doses which are equipotent for venous clot lysis, staphylokinase had a significantly higher potency towards platelet-rich arterial thrombi than streptokinase.

Template bleeding times measured before injection of study drugs averaged 2 to 3 min. Bleeding times did not prolong markedly with staphylokinase or with streptokinase. If anything, the prolongation was somewhat more pronounced with the fibrinogen-sparing streptokinase than with fibrinogen-depleting staphylokinase. Ex vivo platelet aggregation, induced with ADP was unaltered with aspirin and heparin and moderately impaired with streptokinase and with staphylokinase. Platelet aggregation with the combination of epinephrin and arachidonic acid was completely or nearly completely inhibited as a result of the aspirin injection (data not shown). The platelet count did not change significantly in any of the groups. Table 3 shows the template bleeding time, ADP-induced platelet aggregation, platelet count and fibrinogen content (g/l).

Figure 2:
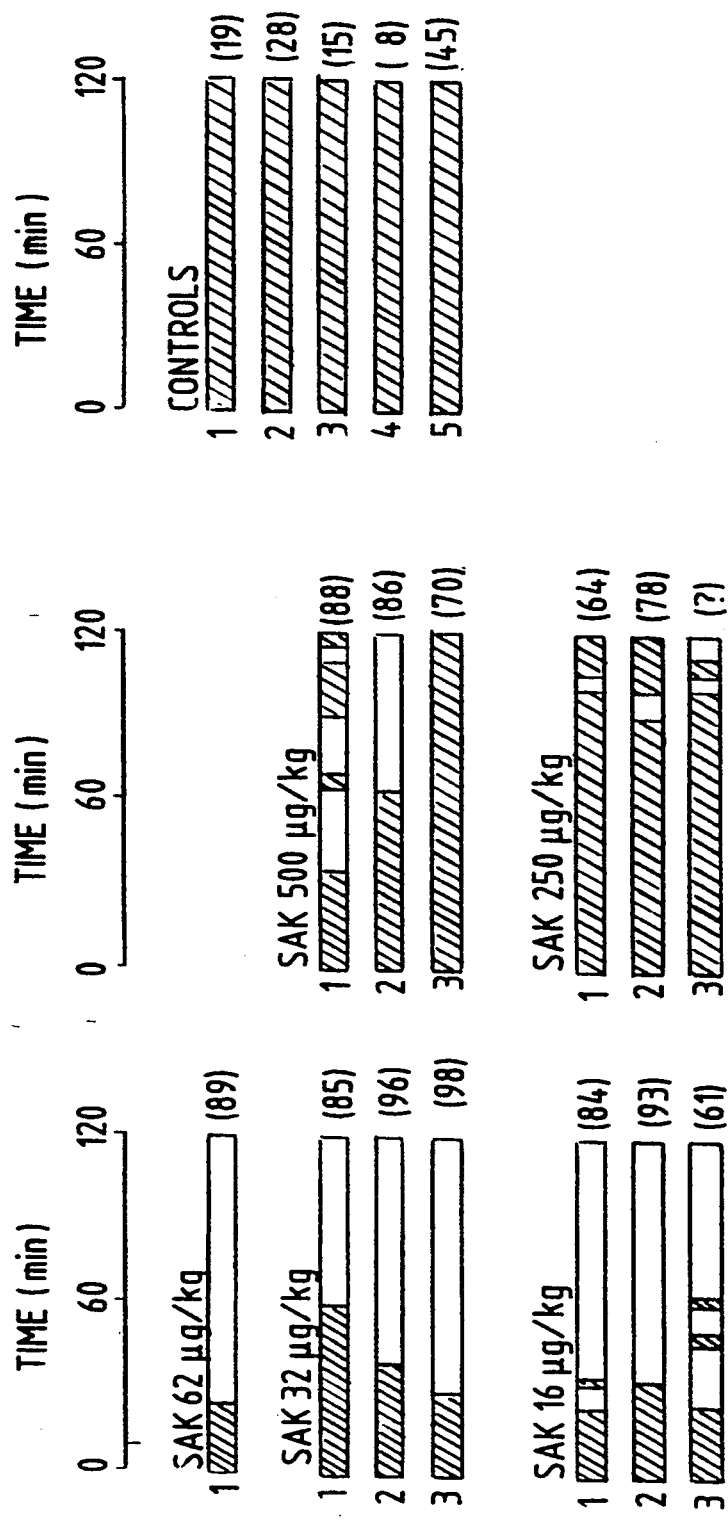
FIG. 2 is a schematic representation of the femoral artery reflow and reocclusion status in dogs with everted femoral arterial grafts, following administration of staphylokinase (SAK), streptokinase (SK) or saline (controls).

FIG. 2 is a schematic representation of the femoral artery reflow and reocclusion status in dogs with everted femoral arterial graft, following administration of staphylokinase (SAK), streptokinase (SK) or saline (controls). Hatched bars represent occlusion, and open bars represent reperfusion. The values indicated between brackets represent venous clot lysis in percent.

EXPERIMENT 3

Staphylokinase/streptokinase test in vitro in plasma

3.1. Human and baboon plasma

A staphylokinase/streptokinase reactivity test in vitro, performed as described in Amery A. et al., Thromb. Diath Haemorrh 9, 175-188, 1963, was applied to human or baboon plasma. Increasing concentrations of staphylokinase or streptokinase (50 µl volumes containing 200 to 100,000 units/ml of streptokinase or 0.2 to 1,000 µg/ml of staphylokinase) were added to 350 µl citrated plasma, immediately followed by addition of 100 µl of a mixture containing thrombin (50 NIH units/ml) and CaCl₂ (25 mM).

In plasma samples obtained from 8 healthy human volunteers, the concentration of staphylokinase required to produce a clot lysis time of 20 min was 1.8±1.1 µg/ml plasma (mean±SD), with individual values ranging from 0.78 to 4.4 µg/ml. Comparative values for streptokinase were 0.50±0.36 µg/ml (mean±SD), with individual values ranging from 0.10 to 1.0 µg/ml. In 14 plasma samples obtained from patients with coronary artery disease, these values were 1.6±0.60 µg/ml (1.0 to 2.0 µg/ml) for staphylokinase and 0.42±0.28 µg/ml (0.14 to 1.0 µg/ml) for streptokinase. In baboon plasma, the concentration of staphylokinase required for clot lysis in 20 min was 2.0±1.0 µg/ml (mean±SD; n=6) with individual values ranging from 2.0 to 4.7 µg/ml. For streptokinase, corresponding values were 68±11 µg/ml (mean±SD; n=9) with individual values ranging from 53 to 93 µg/ml.

The high resistance of baboon plasma against streptokinase persisted after adsorption of pooled plasma with protein A-Sepharose. Furthermore, addition of baboon plasma to human plasma (1:1, vol:vol ratio) did not markedly alter the reactivity of human plasma to streptokinase. This indicates that the high resistance to streptokinase of plasma from animals not previously treated with this drug was not due to the presence of inhibiting substances, but to an intrinsic resistance of the baboon plasma fibrinolytic system to in vitro activation with streptokinase.

Therefore the staphylokinase/streptokinase reactivity test for the detection of staphylokinase- or streptokinase-neutralizing antibodies in baboon plasma was modified using mixtures of 300 µl human plasma and 50 µl buffer, baboon plasma, protein A-Sepharose adsorbed baboon plasma or baboon IgG solution (protein A-Sepharose eluate at acid pH) were used. The plasma clot lysis time was measured and plotted against the concentration of staphylokinase or streptokinase. From this curve the concentration of plasminogen activator that produced complete clot lysis in 20 min was determined. The antibody titers were defined as the difference in the amount of compound required to lyse in 20 min clots composed of mixtures of 300 µl human and 50 µl buffer and those of human plasma with either baboon plasma, protein A-Sepharose adsorbed baboon plasma or baboon IgG solution. The neutralizing antibody titer was expressed in µg per ml or in units per ml of the mixture added to the human plasma. This alternative staphylokinase/streptokinase reactivity test was also applied to dog plasma obtained from animals given either staphylokinase or streptokinase. The baseline neutralizing antibody titer was 39±33 units streptokinase per ml baboon plasma (mean±SD, n=8), whereas no difference for lysis with staphylokinase was observed in mixtures of human plasma with baboon plasma or buffer. In three baboons that were serially assayed, the streptokinase-neutralizing antibody titer increased within 1 week after streptokinase administration to 1,300±1,000 units/ml and decreased to 740±200 units after 3 weeks and to 380±110 units/ml after 6 weeks. The antibody titer of a plasma sample obtained one week after streptokinase administration was reduced from 1,600 units/ml to 10 units/ml by adsorption with protein A-Sepharose, with full recovery of the inhibitory activity in the protein A-Sepharose eluate. In these baboons, staphylokinase-neutralizing antibodies could not be demonstrated after up to four intravenous administrations of 63 µg/kg staphylokinase at 1 to 6 week intervals, using both the original reactivity test as well as the modified staphylokinase reactivity test with the addition of baboon plasma or the protein A-Sepharose eluate referred to above.

Figure 3:
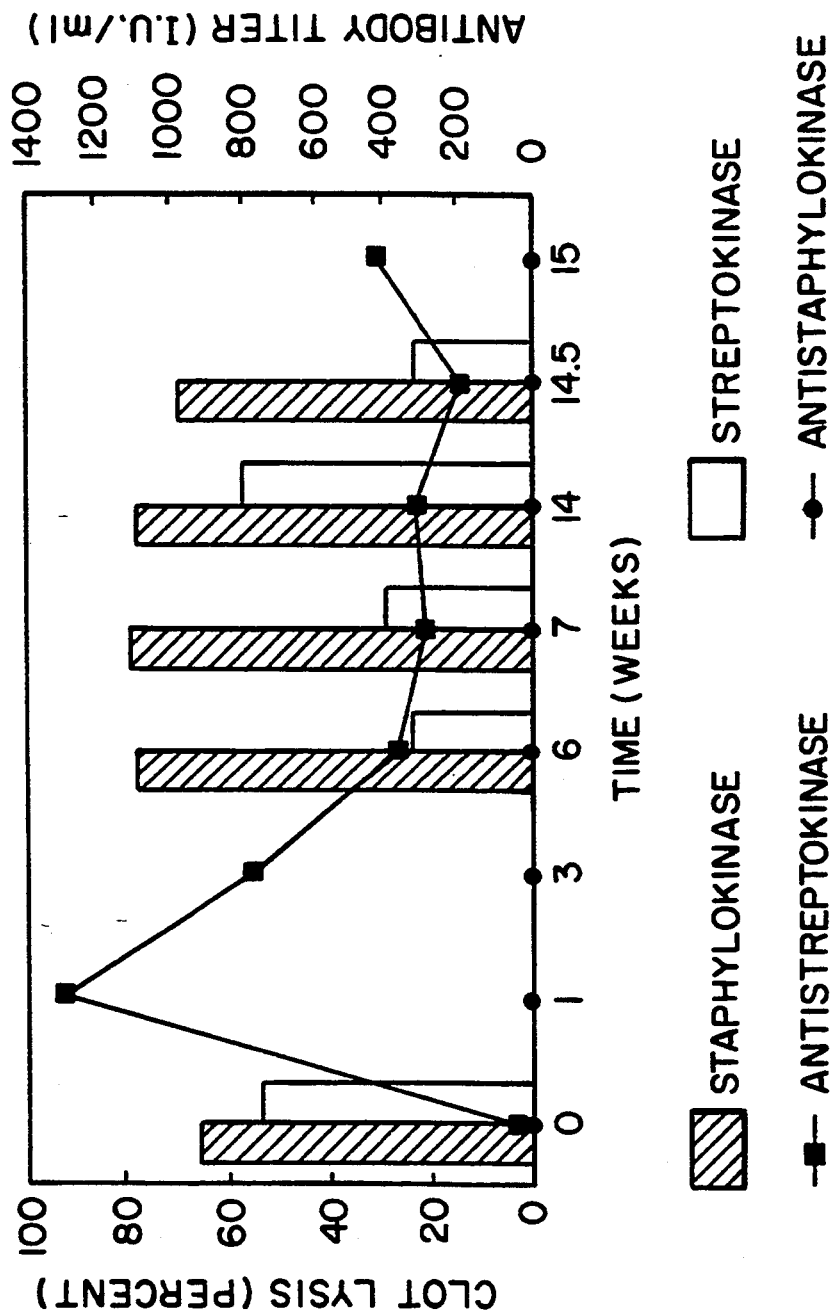
FIG. 3 illustrates in a bar graph the comparative immunogenic effects of staphylokinase and streptokinase in baboons.

The 2 bars (striped and open, respectively) on the left side of FIG. 3 show jugular vein clot lysis following administration of staphylokinase (striped bars) and streptokinase (open bars) to baboons. The bars on the right side show extracorporeal loop results on repeated administration. The antibody titers for staphylokinase (●) and streptokinase (■) are also represented.

3.2. Dog plasma

In pooled dog plasma, the concentration of staphylokinase required for clot lysis in 20 min was 0.17 µg/ml, with a corresponding value for streptokinase of 47 units/ml. With the alternative staphylokinase/streptokinase reactivity test, the streptokinase-neutralizing activity of dog plasma was found to be 73±10 units/ml (n=12). In two dogs given 500 µg/kg streptokinase the titer increased from 68±4 units at baseline to 160±10 units after 9 days (p<0.001) whereas in two dogs given staphylokinase, no significant increase in streptokinase neutralizing antibodies was found at 9 days (75±7 and 90±14 units/ml, respectively, p=0.31). Streptokinase-neutralizing activity was not detected in the Ig fraction (protein A Sepharose eluate) of dog plasma at baseline Or after staphylokinase administration. However, the neutralizing activity induced within 9 days after streptokinase administration was fully recovered in the Ig eluate. With this assay, no staphylokinase-neutralizing activity could be demonstrated in the Ig fraction of dog plasma at baseline or 9 days after administration of 32 µg/kg staphylokinase (data not shown).

EXPERIMENT 4

Jugular vein thrombosis and extracorporeal loop thrombosis models in vivo in the baboon

4.1. Jugular vein thrombosis model

The thrombolytic properties of staphylokinase and streptokinase in vivo were compared in baboons (Papio hamadraeus).

A 0.2 ml $^{125}$I-fibrin labeled autologous whole blood clot was produced in an isolated jugular vein segment using procedures for anesthesia and surgery as described in Collen et al. Circulation 82: 1744–1753, 1990. The plasminogen activators were administered intravenously as a 10 percent slow intravenous injection over 5 min, followed by continuous infusion of the remaining 90 percent dose over 55 min. Thrombolysis was quantitated 30 min after the end of the infusion by determination of the residual radioactivity in the jugular vein segment. Alternatively, the rate of thrombolysis was monitored continuously by external gamma counting, as described previously in Stassen J. M. et al. Fibrinolysis 4 (Suppl 2), 15–21, 1990. Each baboon was used twice with an interval of two days and was randomly assigned to a first infusion with staphylokinase or streptokinase and to a second infusion with the other agent. No surgical procedure failures occurred and the study thus comprised a total of nine baboons. In 4 baboons, the rate of spontaneous clot lysis was followed by external gamma counting for 90 min before infusion of the thrombolytic agent, in order to obtain a background value. Blood samples were taken before the start of the experiment and at 30, 60 and 90 min. These samples were used for measurement of radioactivity, fibrinogen, and α-2-antiplasmin (data not shown). An isotope recovery balance was made by adding the radioisotope content recovered in the vein segments and that in the blood (multiplied with a factor 3 to correct for extravascular distribution) at the end of the experiment.

Dose-response curves following intravenous infusion over 60 min of staphylokinase or streptokinase in baboons with an autologous whole blood clot introduced in the jugular vein were determined (not shown). In 4 control experiments background lysis at 90 min as determined by continuous external gamma counting was 3±1 percent. Systemic infusion of staphylokinase or streptokinase resulted in progressive dose dependent clot lysis. The extent of clot lysis, as determined by ex vivo isotope recovery, was 27±11 percent (n=3) with 32 µg/kg staphylokinase and increased to 68±15 percent (n=3) with a dose of 125 µg/kg, as compared to 37±15 percent (n=3) with 125 µg/kg streptokinase and 67±9 percent (n=3) with 500 µg/kg streptokinase. The isotope recovery balance ranged between 86±10 and 97±3 percent (data not shown), confirming that no significant parts of the clot were lost by embolization. Fibrinogen and α$_2$-antiplasmin levels did not decrease in any of the groups. The activated partial thromboplastin times prolonged from a baseline value of 58±13 (mean±SEM, n=18) to >3 min. determined at 60 and 90 min. after the start of the staphylokinase or streptokinase infusion in all animals (data not shown).

Continuous external gamma counting showed sigmoidal lysis versus time curves, characterized by a slow initial lysis, acceleration during the second half of the infusion period and a levelling-off during the 30 min observation period after the end of the infusion. The shapes of the curves obtained with staphylokinase and streptokinase at comparable molar concentrations were very similar.

Fitting of the dose-response data of clot lysis at 90 min with the exponentially transformed sigmoidal function yielded values for b, z and c. The thrombolytic potency of staphylokinase tended to be somewhat higher than that of streptokinase, as revealed by a lower b-value and by a higher z-value. With the ex vivo isotope recovery method b values were 0.037±0.008 and 0.11±0.03 mg/kg for staphylokinase and streptokinase respectively (p=0.024) and z values were 1,500±850 and 270±120 percent lysis per mg/kg respectively (p=0.16). The corresponding values, obtained by external gamma counting, were 0.037±0.014 and 0.14±0.05 mg/kg respectively (p=0.06) for the b-values and 1,800±2,100 and 170±96 percent lysis per mg/kg respectively (p=0.45) for the z-values. However, in view of the differences in molecular weight between staphylokinase and streptokinase, their thrombolytic potencies on a molar basis were virtually identical.

4,2. Extracorporeal loop thrombosis model

The thrombolytic properties of repeated infusions of staphylokinase or streptokinase in vivo were also compared in baboons (Papio hamadraeus) with a combined 0.3 ml $^{125}$I-fibrin labeled autologous plasma clot and a 0.3 ml $^{125}$I-fibrin labeled pooled baboon plasma clot, inserted into an extracorporeal arteriovenous loop.

An exposed anterior tibial artery was therefore catheterized with a 4 French catheter (Portex White, Portex, Hythe, U.K.) and connected via two hypodermic syringes to a catheterized brachial vein. The blood flow through the extracorporeal loop was maintained at 10 ml/min with a peristaltic pump. The clot from pooled baboon plasma was introduced in the proximal syringe and the clot from autologous plasma in the distal syringe. The plasma clots were prepared by mixing 0.3 ml plasma with a trace amount (approximately 1.5 µCi) $^{125}$I-labeled human fibrinogen solution (Amersham, Buckinghamshire, U.K.), 0.07 ml of a mixture of bovine thrombin (15 NIH units/ml) and 0.5 M CaCl$_2$, and incubation for 30 min at 37° C. Thirty min before the start of the infusion, 7.5 mg/kg ridogrel (a combined thromboxane synthase inhibitor and prostaglandin endoperoxide receptor antagonist) was administered as an intravenous bolus to prevent platelet deposition in the extracorporeal loop. The baboons were anticoagulated with heparin (300 units/kg followed by a continuous infusion of 60 units/kg per hour throughout the experiment). The animals were randomly allocated to infusion with 63 µg/kg staphylokinase or with 250 µg/kg streptokinase over I hour followed 30 min after the end of the infusion by a second infusion with the other agent. During the interval between the two infusions, the labeled plasma clots in the extracorporeal loop were replaced with fresh clots. The thrombolytic agents were given intravenously as a 10 percent bolus and a 90 percent infusion over 1 hour.

In three baboons, staphylokinase and streptokinase administration was repeated at 6 weeks, 7 weeks, 14 weeks and 14½ weeks after the first administration. In these animals lysis with 63 µg/kg staphylokinase and 250 µg/kg streptokinase was measured of plasma clots introduced in an extracorporeal arteriovenous loop (data not shown). Lysis with 63 µg/kg staphylokinase was 66±7 percent (mean±SEM, n=3) in the jugular vein model and 78±6, 80±5, 78±1 and 70±9 percent in the extracorporeal loop determined at 6, 7, 14 and 14½ weeks after the first administration, respectively. These values were not significantly different. Lysis with 250 µg/kg streptokinase in the jugular vein model was 54±5 percent (n=3) and 24±8, 29±9, 57±2 and 23±7 percent in the extracorporeal loop after 6, 7, 14 and 14½ weeks, respectively. The difference between the baseline jugular vein clot lysis and the extracorporeal clot lysis at 6 weeks was significant (p=0.04). Between the 7th and 14th week the reactivity to streptokinase recovered significantly from 29±9 to 57±2 percent (p=0.03) to become similar to the baseline jugular vein clot lysis value, but at 14½ week, which is at 3 days after a renewed streptokinase administration, clot lysis with 0.25 mg/kg streptokinase was again significantly reduced (from 57±2 to 23±7 percent (p=0.003)).

The 4 pairs of bars on the right side of FIG. 3 represent the results of the plasma clot lysis experiments in the extracorporeal loop model following repeated administration of staphylokinase (striped bars) and streptokinase (open bars) to baboons. The antibody titers for staphylokinase (●) and streptokinase (■) are also represented. The figure shows very clearly the higher clot lysis potency and lower antibody titer for staphylokinase as compared to streptokinase.

These data demonstrate that streptokinase administration in baboons, as observed in man, induces neutralizing antibody formation with associated resistance to clot lysis with renewed administration. No neutralizing antibodies could be demonstrated in human or baboon plasma, no induction of neutralizing antibodies with staphylokinase administration could be documented and clot lysis with repeated administration of staphylokinase remained unaltered.

The above examples show that in comparison to streptokinase staphylokinase can be a potent plasminogen activator towards platelet-rich clots as found in arterial thrombotic diseases, such as myocardial infarction, and does not induce antibody production so that repeated administration is possible.

TABLE 1

| | Dose (µg/kg) | lysis at 90 min. (percent) | Residual fibrinogen (percent) | Residual $\alpha_2$-antiplasmin (percent) | Curve fitting parameters | | |
|---|---|---|---|---|---|---|---|
| | | | | | n | z | b |
| A. Platelet-poor human plasma clot | | | | | | | |
| Saline | — | 25 ± 1 (96) | 140 ± 5 (61) | 110 ± 3 (68) | | | |
| Staphylokinase | 3 | 37 ± 4 (3) | 130 ± 5 (3) | 100 ± 6 (3) | 108 | 1,100 ± 200 | 0.018 ± 0.006 89 |
| | 9 | 33 ± 3 (3) | 170 ± 4 (3) | 150 ± 41 (3) | | | |
| | 27 | 55 ± 7 (3) | 180 ± 26 (3) | 120 ± 10 (3) | | | |
| | 80 | 86 ± 2 (3) | 170 ± 19 (3) | 140 ± 14 (3) | | | |
| Streptokinase | 3 | 37 ± 5 (3) | 180 ± 14 (3) | 110 ± 6 (3) | 117 | 1,800 ± 130 | 0.012 ± 0.004 100 |
| | 9 | 57 ± 8 (3) | 170 ± 16 (3) | 120 ± 23 (3) | | (p = 0.003) | (p = 0.300) |
| | 27 | 65 ± 7 (3) | 160 ± 32 (3) | 83 ± 3 (3) | | | |
| | 80 | 73 ± 9 (7) | 130 ± 5 (3) | 69 ± 9 (7) | | | |
| | 160 | 91 ± 1 (3) | 150 ± 3 (3) | 62 ± 16 (3) | | | |
| B. Platelet-rich human plasma clot (300,000/µl) | | | | | | | |
| Saline | — | 18 ± 2 (25) | 160 ± 13 (13) | 95 ± 5 (14) | | | |
| Staphylokinase | 27 | 38 ± 17 (3) | 110 ± 7 (3) | 150 ± 8 (3) | 37 | 1,100 ± 140 | 0.033 ± 0.001 100 |
| | 55 | 90 ± 1 (3) | 100 ± 8 (3) | 99 ± 6 (3) | | | |
| | 90 | 75 ± 9 (6) | 120 ± 9 (3) | 110 ± 5 (3) | | | |
| Streptokinase | 27 | 34 ± 4 (3) | 120 ± 15 (3) | 130 ± 14 (3) | 34 | 1,300 ± 75 | 0.032 ± 0.002 100 |
| | 55 | 87 ± 3 (3) | 120 ± 10 (3) | 100 ± 2 (3) | | (p = 0.224) | (p = 0.648) |
| | 80 | 90 ± 1 (3) | 94 ± 4 (3) | 62 ± 21 (3) | | | |
| C. Platelet-enriched human plasma clot (1,500,000/µl) | | | | | | | |
| Saline | — | 19 ± 4 (5) | 110 ± 15 (3) | 140 ± 33 (5) | | | |
| Staphylokinase | 27 | 23 ± 3 (3) | 120 ± 3 (3) | 100 ± 3 (3) | 14 | 900 ± 180 | 0.044 ± 0.01 91 |
| | 80 | 76 ± 10 (3) | 120 ± 6 (3) | 150 ± 26 (3) | | | |
| | 160 | 88 ± 1 (3) | 120 ± 15 (3) | 67 ± 33 (3) | | | |
| Streptokinase | 80 | 30 ± 4 (4) | 140 ± 10 (4) | 120 ± 5 (4) | 18 | 160 ± 73 | 0.11 ± 0.07 69 |
| | 250 | 55 ± 14 (5) | 140 ± 16 (5) | 99 ± 10 (5) | | (p < 0.001) | (p = 0.417) |
| | 500 | 69 ± 11 (4) | 140 ± 25 (4) | 75 ± 18 (4) | | | |

The data represent mean ± SEM of the number of experiments indicated between brackets.

TABLE 2

| Agent | Dose (μg/kg) | Number of dogs | Femoral arterial eversion graft thrombus ||||||| Femoral vein clot ||
| | | | Blood flow (% of baseline) ||| Time to reflow(*) (min) | Femoral arterial patency status(**) ||| Clot lysis (percent) | Isotope recovery (percent) |
| | | | after clamp release | 1 h after drug | 2 h after drug | | PO | CR | PP | | |
| --- | --- | --- | --- | --- | --- | --- | --- | --- | --- | --- | --- |
| Controls | — | 5 | 20 ± 4 | 0 | 0 | — | 5 | 0 | 0 | 23 ± 6 | 86 ± 6 |
| Staphylokinase | 16 | 3 | 29 ± 10 | 30 ± 5 | 65 ± 10 | 30 ± 3 | 0 | 1 | 2 | 79 ± 10 | 103 ± 5 |
| | 32 | 4(***) | 32 ± 7 | 49 ± 17 | 52 ± 15 | 36 ± 9 | 0 | 0 | 4 | 92 ± 3 | 108 ± 2 |
| Streptokinase | 250 | 3 | 23 ± 2 | 0 | 8 ± 8 | 97 ± 3 | 0 | 3 | 0 | 71 ± 6 | 103 ± 3 |
| | 500 | 3 | 26 ± 7 | 7 ± 7 | 10 ± 10 | 72 ± 25 | 1 | 1 | 1 | 81 ± 6 | 102 ± 1 |

The data represent mean ± SEM
(*) In animals with persistent occlusion, the reflow time was assigned a value at 120 min. for calculation of the mean ± SEM.
(**) PO: persistent occlusion; CR: cyclic reocclusion and reflow after inital reflow; PP: persistent patency after initial ref
(***) Includes one dog given 62 μg/kg with results indistinguisable from the three dogs given 32 μg/kg.

TABLE 3

| Agent | Dose (μg/kg) | Bleeding time (min) ||| ADP-induced platelet aggregation (%) ||| platelet count ($\times 10^3/mm^3$) |||
| | | baseline | 1 h after drug | 2 h after drug | baseline | 1 h after drug | 2 h after drug | baseline | 1 h after drug | 2 h after drug |
| --- | --- | --- | --- | --- | --- | --- | --- | --- | --- | --- |
| Controls | — | 1.6 ± 0.2 | 2.7 ± 0.4 | 2.1 ± 0.2 | 47 ± 7 | 42 ± 11 | 35 ± 10 | 340 ± 60 | 380 ± 10 | 390 ± 10 |
| Staphylokinase | 16 | 3.2 ± 0.1 | 2.3 ± 0.3 | 3.7 ± 0.7 | 60 ± 5 | 42 ± 13 | 24 ± 12 | 560 ± 50 | 510 ± 40 | 500 ± 70 |
| | 32(*) | 2.5 ± 0.5 | 4.5 ± 0.9 | 2.8 ± 0.5 | 60 ± 1 | 18 ± 3 | 10 ± 7 | 480 ± 60 | 420 ± 70 | 470 ± 40 |
| Streptokinase | 250 | 2.5 ± 0.3 | 3.3 ± 0.9 | 3.3 ± 0.3 | 65 ± 6 | 38 ± 3 | 43 ± 11 | 440 ± 40 | 450 ± 40 | 450 ± 20 |
| | 500 | 1.8 ± 0.2 | 7.7 ± 2.3 | 5.0 ± 2.0 | 57 ± 3 | 30 ± 12 | 39 ± 8 | 480 ± 30 | 430 ± 20 | 480 ± 50 |

| Agent | Dose (μg/kg) | n | fibrinogen (g/l) |||||
| | | | baseline | 30 min. | 1 h | 2 h | 24 h |
| --- | --- | --- | --- | --- | --- | --- | --- |
| Controls | — | 5 | 1.4 ± 0.1 | — | 1.8 ± 0.1 | 1.9 ± 0.1 | 2.0 ± 0.1 |
| Staphylokinase | 16 | 3 | 1.8 ± 0.7 | 1.8 ± 0.6 | 1.3 ± 0.7 | 0.2 ± 0.1 | 1.2 ± 0.1 |
| | 32(*) | 4 | 1.0 ± 0.2 | 0.9 ± 0.1 | <0.1 | <0.1 | 1.0 ± 0.2 |
| Streptokinase | 250 | 3 | 1.2 ± 0.3 | 1.1 ± 0.3 | 1.1 ± 0.3 | 1.1 ± 0.3 | — |
| | 500 | 3 | 2.0 ± 0.4 | 2.0 ± 0.5 | 1.7 ± 0.3 | 1.8 ± 0.4 | 1.8 ± 0.2 |

The results are taken as mean ± SEM
(*)Includes one dog given 62 μg/kg with results indistinguisable from the other three dogs.

We claim:

1. A method for treating arterial thrombosis attributable to at least one platelet-rich thrombus comprising administering an amount of staphylokinase, effective to treat arterial thrombosis attributable to at least one platelet-rich thrombus, to a human for which such treatment is indicated, said amount comprising between 0.05 and 10 mg. per kilogram body weight of said human.

2. The method according to claim 1 wherein the method further comprises administering intravascularly an amount of staphylokinase, effective to treat myocardial infarction attributable to at least one platelet-rich thrombus, to a human for which myocardial infarction treatment is indicated.

3. The method according to claim 1 wherein the method further comprises administering intravascularly an amount of recombinant staphylokinase, effective to treat arterial thrombosis attributable to at least one platelet-rich thrombus, to a human for which such treatment is indicated.

* * * * *